United States Patent [19]

Redikultsev et al.

[11] Patent Number: 4,686,189

[45] Date of Patent: Aug. 11, 1987

[54] APPARATUS FOR BIOCONVERSION OF VEGETAL RAW MATERIAL

[76] Inventors: Jury V. Redikultsev, mikroraion "G", 19, kv. 113; Leonid A. Litvinenko, mikroraion "AB", 8 kv. 74; Evgeny L. Golovlev, mikroraion "V", 28, kv. 24; Ljudmila A. Golovleva, mikroraion "V", 28, kv. 24; Dmitry N. Chermensky, mikroraion "G", 7, kv. 67, all of Puschino, Moskovskaya oblast; Georgy K. Skryabin, ulitsa Ulyanova, 3, kv. 124, Moscow, all of U.S.S.R.

[21] Appl. No.: 651,050

[22] Filed: Sep. 14, 1984

[30] Foreign Application Priority Data

Sep. 21, 1983 [SU] U.S.S.R. ............... 3640901

[51] Int. Cl.⁴ .................... C12M 1/36
[52] U.S. Cl. .................... 435/289
[58] Field of Search ........... 435/287, 289, 292, 293, 435/299, 302, 311, 313, 315, 316

[56] References Cited

U.S. PATENT DOCUMENTS

| | | | |
|---|---|---|---|
| 46,809 | 3/1865 | Martin | 435/311 X |
| 1,000,086 | 8/1911 | Goetz et al. | 435/311 X |
| 1,896,811 | 2/1933 | Currie et al. | 435/287 X |
| 4,062,276 | 12/1977 | Stahmann | 99/467 |

FOREIGN PATENT DOCUMENTS

| | | | |
|---|---|---|---|
| 587147 | 1/1978 | U.S.S.R. | 435/311 |
| 1000415 | 2/1983 | U.S.S.R. | 435/313 |

OTHER PUBLICATIONS

Microbial Fermentation Preparations, Processes and Equipment, Moscow, the "Pischevaya Promyshlennest" Publishers 9/1979, pp. 195–196.

Summary of Reports of the All–Union Symposium on Bioconversion of vegetal Raw Material, Apr 12 to 16, 1982, vol. 2, (pp. 184 and 185), Riga, 4/1982.

USSA–"Tsentralny Protsessor M2, Tekhnicheskoe Opisanie I Instruktsiya Po Eksplutatsii"; Published by the "Elektronika" Research and Development Institute 4/1979, pp. 10 and 11.

Primary Examiner—Samuel Scott
Assistant Examiner—Allen J. Flanigan
Attorney, Agent, or Firm—Lilling & Greenspan

[57] ABSTRACT

An apparatus for bioconversion of vegetal raw material comprises a bioreactor communicable with a means for charging this material and discharging the end product. A pressure-sealed chamber for storing excess liquid displaceable from the bioreactor is provided with a liquid level control means and connected to a source of compressed air, atmosphere, inoculator, steam source and bioreactor. A distributor of gas-steam, gas-liquid flows and a flow of inoculum is connected to the liquid level control means and inoculator. Feeders are disposed inside the bioreactor at various levels in terms of height thereof and connected to the flow distributor, a pump being provided between the bioreactor and steam source. A control unit is electrically connected with the bioreactor, steam source, inoculator, compressed air source, a pressure-sealed chamber, flow distributor, and pump.

4 Claims, 1 Drawing Figure

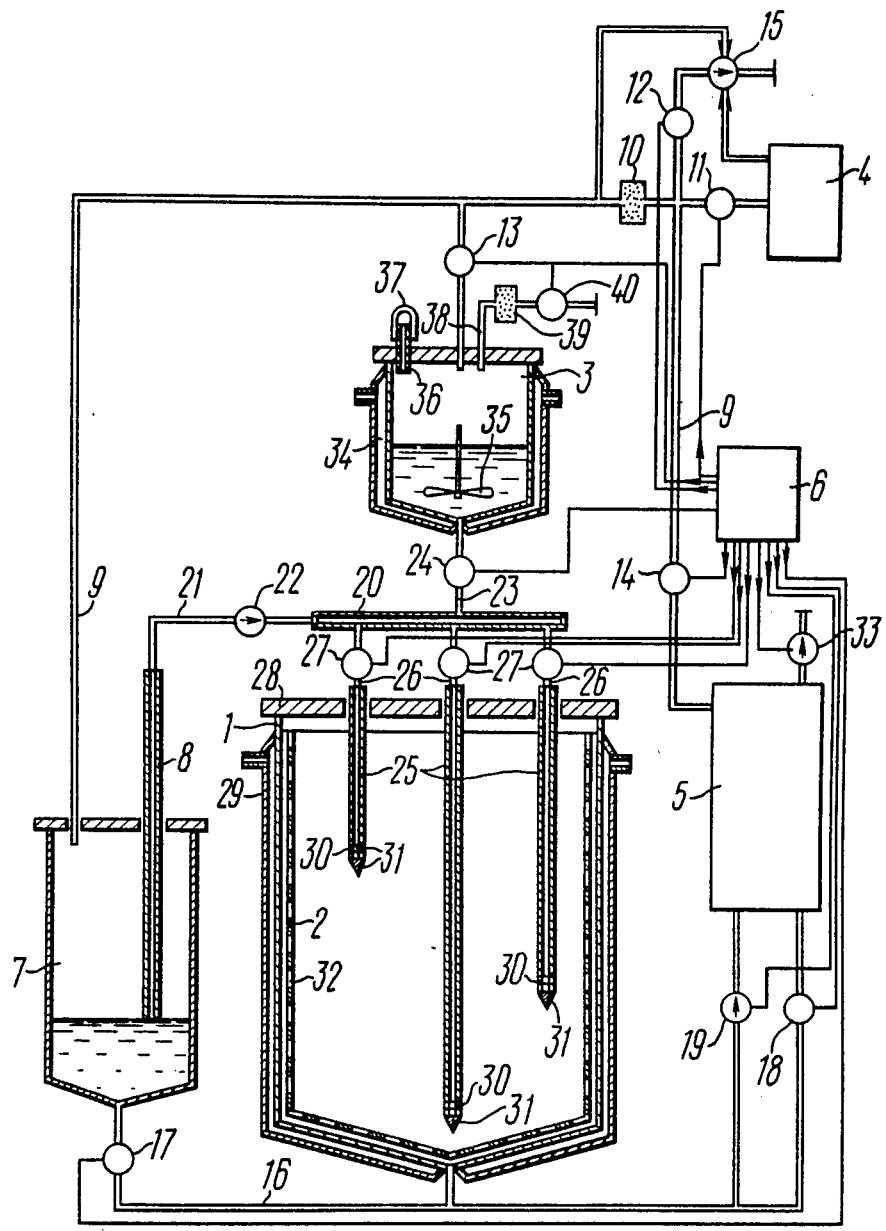

APPARATUS FOR BIOCONVERSION OF VEGETAL RAW MATERIAL

FIELD OF THE INVENTION

This invention relates generally to apparatus for cultivating microorganisms on solid nutrient substrates, and more particularly it concerns apparatus for bioconversion of vegetal raw materials.

The present invention can find application in microbiology for producing vegetable proteins, aminoacids, ferments, substances for biological protection of plants, bacterial fertilizers, etc. The invention can also be utilized in the pharmaceutical practice to produce vitamins, antibiotics, hormones, toxins and other preparations by bacterial transformation making use of immobilized cells of microorganisms, as well as in the chemical industry for obtaining various acids, carrying out oxidation and reduction reactions and the like. The proposed apparatus can further be used with success in agriculture for utilizing with a greater advantage the locally grown vegetal raw materials and transforming farm side products into high-protein fodder rich in aminoacids.

BACKGROUND OF THE INVENTION

In the present-day industrial processes bioconversion of vegetal raw materials is carried out in bioreactors where the material is spread on perforated shelves or in bioreactors making use of mechanical stirrers.

DESCRIPTION OF THE PRIOR ART

There is known a mechanized apparatus for growing microorganisms in a thick bed of nutrient medium (cf., K. A. Kalunyants and L. I. Golger "Mikrobnye fermentnye preparaty" - Microbial Ferment Preparations, in Russian, the "Pischevaya promyshlennost" publishers, Moscow, 1979).

This apparatus comprises a bioreactor in the form of a substantially vertical cylinder separated into sections by perforated plates and provided in its upper portion by a port for charging the vegetal raw material and introducing inoculum. The vegetal raw material is arranged in layers on the perforated plates. Inside the bioreactor in each of the sections there is provided a stirring means intended for maintaining a preselected level of the layer and ensuring air distribution to prevent stagnation of the material in each section.

The bioreactor is hermetically connected to a steam source and a source of compressed air fed to each section at a predetermined temperature to the undersides of the perforated plates.

Heat transfer and bioconversion takes place in the layers, each of these layers of the vegetal raw material being vigorously aerated.

The end product is delivered to the lower tapered sections of the bioreactor to be discharged into a receiving hopper.

However, the above construction of the bioreactor requires much metal to be consumed for its manufacture. Another disadvantage is that only part of the entire volume of the bioreactor is utilized when it is loaded with the vegetal raw material, resulting in low efficiency of the apparatus.

There is also known an apparatus for bioconversion of vegetal raw material (cf., "Bioreaktor dlya tverdofaznoi fermentatsii" - Bioreactor for Solid Phase Fermentation, in Russian, U. E. Viestur, et al "Tezisy dokladov - Biokonversiya rastitelnogo syrya" vol. 2, p. 184, Riga, 1982) which comprises a bioreactor communicating with a means for charging the vegetal raw material and discharging the end product and connected by pipelines to an inoculator, a compressed air source and a steam source.

The bioreactor is fashioned as a substantially cylindrical vessel having a bottom and a cover plate in the form of truncated cones and provided with a heat-transfer jacket. Inside the vessel coaxially therewith there is arranged a diffuser/heat-exchanger accommodating a mixing means in the form of a worm and stirrer providing for stirring the vegetal raw material and heat- and mass-transfer of the microorganisms of fungi mycelium being grown.

The means for charging the vegetal raw material and discharging the end product is fashioned as a reversible screw conveyer.

Prior to operation, the bioreactor is loaded with a vegetal raw material to a level not exceeding the upper edge of the diffuser/heat-exchanger.

Thereafter, the bioreactor is sterilized by saturated steam fed from the source of steam to the heat-transfer jacket and diffuser/heat-exchanger.

Subsequent to the sterlization, an inoculum, particularly a fungi mycelium, is introduced to the vegetal raw material, and the control unit is loaded with predetermined parameters for operation of the stirring means, maintaining the flow rate of compressed air, temperature control range, and pH value in the bioreactor, and controlling the end - of - operation time for discharging the end product.

In the course of bioconversion the rotating worm captures the vegetal raw material which acts as a nutrient substrate for the mycelium fungi and carries it upwards to flow over the edge of the diffuser/heat-exchanger. In this manner heat- and mass-transfer of the mycelium being cultivated and its uniform distribution throughout the body of the nutrient substrate are ensured.

The worm and the stirrer are rotated in the opposite directions upon pulsewise energization by the control unit. Compressed air for aeration of the fungi mycelium is delivered to the bioreactor from the source of compressed air through the bacterial filters.

On expiration of the predetermined dwelling time required for carrying out the process of bioconversion, the screw conveyer for discharging the end product enriched with fungi protein is actuated.

However, the bioreactor is loaded with the vegetal raw material to not more than half its volume, since it is impossible to fully load the bioreactor due to the provision therein of the diffuser/heat-exchanger and the stirring means capable of normal functioning only at partial loading of the bioreactor with the vegetal raw material. This in turn affects the efficiency of the apparatus and requires additional power consumption for the bioconversion process due to the operation of the stirring means.

It further has to be noted that the use in the bioreactor of a stirring means disturbs the structure of the fungi mycelium growing in the body of the vegetable raw material to cause additional time expenditures connected with reestablishment of the thus broken structure, which also makes the apparatus less efficient.

SUMMARY OF THE INVENTION

It is therefore an object of the present invention to ensure a uniform heat- and mass-transfer throughout the volume of the bioreactor and, consequently, to improve the efficiency of an apparatus for bioconversion of a vegetable raw material.

The objects of the invention are attained by an apparatus for bioconversion of vegetal raw material comprising a bioreactor communicating with a means for charging this material and discharging the end product, and connected by pipes to an inoculator, a source of compressed air and a source of steam producing gas-steam, liquid-steam flows and a flow of inoculum and electrically connected with a control unit. According to the invention, the apparatus includes a pressure-sealed chamber for storing excess liquid displaceable from the bioreactor provided with a liquid level control means and connected by a pipe for conveying the gas-steam flows having valves to the source of compressed air, atmosphere, inoculator and the source of steam, and connected by a pipe for conveying the gas-liquid flows having valves to the bioreactor and the source of steam; a distributor of the gas-steam, gas-liquid flows and the flow of inoculum connected by a pipe having a non-return valve to the liquid level control means and by another pipe having a valve to the inoculator; feeders disposed inside the bioreactor at different levels in terms of its height and connected by pipes having valves to the distributor of the gas-steam, gas-liquid flows and the flow of inoculum; a pump for circulating the gas-steam and gas-liquid flows provided between the bioreactor and the source of steam; and, a control unit being connected by its corresponding outputs to the valves provided in the pipes communicating the pressure-sealed chamber with the source of compressed air, atmosphere, inoculator, source of steam and bioreactor, and to the valves provided in the pipes connecting the distributor of gas-steam, gas-liquid flows and the flow of inoculum to the inoculator and feeders, and to the pump.

Preferably, the apparatus for bioconversion of vegetal raw material is fashioned as a tube an end of which is immersible in the bioreactor and has radially extending holes, the face of this end being plugged by a cover cap.

Advisably, in the proposed apparatus for bioconversion of vegetal raw material the means for charging this material and discharging the end product is fashioned as a container installed inside the bioreactor and having perforated walls and bottom for preventing compaction of the vegetal raw material by the gas-steam, gas-liquid flows and the flow of inoculum admitted thereto through the feeders, the cross-sectional area of the perforations in the walls and bottom of the container being smaller than the size of particles of the vegetal raw material.

The proposed apparatus is simple to fabricate and requires less metal to be consumed for its manufacture than the prior art apparatus. The absence of a mechanical stirrer in the bioreactor ensures that the bioreactor can be fully loaded with the vegetal raw material, which results in a higher efficiency of the apparatus and reduced power consumption for its operation.

Heat and mass transfer necessary for carrying out the process of bioconversion is executed by exerting a hydrodynamic action on the vegetal raw material by the gas-liquid flows penetrating through the entire volume of the bioreactor. This obviates time losses associated with reestablishing the structure of the nutrient substrate usually disturbed when mechanical stirring means are employed, thus making the apparatus still more efficient.

Provision is envisaged in the proposed apparatus for replaceable containers having perforated walls and bottom for charging the vegetal raw material and discharging the end product, such a provision enabling to preserve the structure of the nutrient substrate, reduce the amount of time required for loading the bioreactor, as well as for transportation of the vegetal raw material and the end product.

BRIEF DESCRIPTION OF THE DRAWINGS

The invention will now be described in greater detail with reference to a preferred emodiment thereof taken in conjunction with the accompanying drawing, in which there is schematically represented an apparatus for bioconversion of vegetal raw material according to the invention (a longitudinal sectional view of a bioreactor, pressure-sealed chamber and inoculator).

DETAILED DESCRIPTION OF THE INVENTION

An apparatus for bioconversion of vegetal raw material comprises a bioreactor 1 communicating with a means 2 for charging such material and discharging the end product, and connected by a system of pipes to an inoculator 3, a source 4 of compressed air, and a source 5 of steam, which provide gas-steam, gas-liquid flows and a flow of inoculum and are electrically connected to a control unit 6. The apparatus also comprises a pressure-sealed chamber 7 for storing excess liquid forced out of the bioreactor 1 and which is provided with a liquid level control means 8. The chamber 7 is connected by a pipe 9 to the compressed air source 4, the atmosphere, the inoculator 3 and the steam source 5, this pipe having arranged thereon a bacterial filter 10 and valves 11, 12, 13 and 14. A pressure regulator 15 for maintaining a preselected pressure in the apparatus is provided in the pipe 9 before its outlet. The chamber 7 also communicates by way of a pipe 16 for conveying gas-liquid flows to the bioreactor 1 and the steam source 5, this pipe 16 having valves 17 and 18.

A pump 19 is further provided for circulating the gas-steam and gas-liquid flows between the bioreactor 1 and the steam source 5.

A distributor 20 of the gas-steam and gas-liquid flows and the flow of the inoculate is connected by a pipe 21 having a non-return valve 22 to the liquid level control means 8 and by a pipe 23 having a valve 24 to the inoculator 3.

Installed in the bioreactor 1 at different levels in terms of its height are feeders 25 connected by pipes 26 to the flow distributor 20, the number of these pipes 26 being equal to the number of feeders 25, these pipes 26 being provided with valves 27. The bioreactor 1 is enclosed by a cover plate 28 and provided with a jacket 29.

Each feeder 25 is generally a tube immersed in the vegetal raw material, an end portion of the feeders having radial holes 30 and the end face of these feeders 25 being plugged by caps 31. To facilitate immersion of the feeders 25 in the vegetal raw material, the caps 31 are cone-shaped.

The means 2 for charging the vegetal raw material and discharging the end product is fashioned as a container (hereinafter referred to as container 2) disposed inside the bioreactor 1 and having perforated walls and bottom for preventing compaction of the material when the flows of gas, steam, liquid and inoculator are conveyed through the feeders 25. The size of perforations 32 in the container 2 is less than the size of particles of the vegetal raw material.

The container 2 having the perforated walls and bottom in the herein described modification conforms in shape to the shape of the bioreactor 1, which assures a more complete occupation of the bioreactor 1 with the vegetal raw material.

The steam source 5 in the form of a steam generator (hereinafter referred to as steam generator 5) is provided with a steam trap 33.

The inoculator 3 is generally a gas-tight vessel provided with a heat transfer jacket 34 and a stirrer 35 arranged inside the vessel. A pipe 36 having a cover cap 37 is provided for introducing inoculation material to the inoculator 3. In order to ensure independent aeration of the inoculum, the inoculator 3 is communicated with the atmosphere by way of a pipe 38, on which there are disposed a bacterial filter 39 and a valve 40.

The control unit 6 has a suitable conventional construction described, for example, in the publication "Tsentralny protsessor M2, Tekhnicheskoe opisanie i instruktsiya po ekspluatatsii"; published by the "Elektronika" Research and Development Institute 1979, pp. 10 and 11.

The control unit 6 generates signals to open and close all the valves 11, 12, 13, 14, 17, 18, 24, 27 and 40, as well as to energize and deenergize the pump 19 to assure circulation of the gas-steam, gas-liquid flows and the flow of inoculum.

The proposed apparatus for bioconversion of vegetal raw material operates in the following manner.

The container 2 is charged with a vegetal raw material, such as wheat straw or birch-tree saw dust, installed inside the bioreactor 1, and closed by the cover plate 28. Thereafter, the feeders 25 are introduced through the holes in the cover cap 28 to the vegetal raw material at various levels in terms of height of the bioreactor 1 to provide for uniform delivery of the gas-steam, gas-liquid flows and the flow of inoculum through the holes 30 to the entire body of the vegetal raw material.

The pipes 26 are connected to the feeders 25 to thereby pressure-seal the bioreactor 1.

A distilled water or a nutrient solution is placed into the steam generator 5, and a program is preset at the control unit 6 to assure the process of sterilization of the vegetal raw material. In consequence, the control unit 6 generates signals for opening the valves 13, 14, 24, closing the valves 11, 12, 18, 40, and actuating the valves 17 and 27 in antiphase. At the same time, the pump 19 and a heater (not shown) of the steam generator 5 are actuated.

Subjected to heating, the distilled water occupying the steam generator 5 tends to boil and produce steam which is conveyed along the pipe 9 through the valve 14, bacterial filter 10 and valve 13 to the inoculator 3, wherefrom it is delivered through the pipe 23 via the valve 24, distributor 20 of gas-steam, gas-liquid and inoculum flows and further along the pipes 26 through the valves 27, feeders 25 and holes 30 to enter the vegetal raw material occupying the bioreactor 1. Simultaneously, the steam flows along the pipe 9 to the pressure-sealed chamber 7 wherefrom part of the steam is conveyed through the liquid level control means 8 along the pipe 21 via the non-return valve 22, flow distributor 20 along further along the pipes 26 through the valves 27, feeders 25 and holes 30 to the vegetal raw material.

During sterlization of the vegetal raw material the pressure of the air occupying the apparatus tends to rise, this air tending to escape to the atmosphere through the steam trap 33. When the air is completely forced out of the apparatus, the steam trap 33 closes, whereby the dwelling time for sterilization of the vegetal raw material determined by the program starts.

When entering the bioreactor 1, the steam tends to condense on the vegetal raw material to extract therefrom soluble components and produce a steam-liquid mixture which is pumped from the bioreactor 1 by the pump 19 along the pipe 16 to be conveyed to the steam generator 5, where it is again subjected to vaporization.

Upon expiration of the dwelling time for sterilization of the vegetal raw material as preset by the program, the heater of the steam generator 5 is deenergized, the valves 13, 14 and 27 are closed, the pump 19 is switched off, and the valve 18 is opened. Therewith, the extract formed in the course of sterilization of the vegetal raw material is conveyed through the valve 18 from the steam generator 5 along the pipe 16 to the bioreactor 1, and through the valve 17 it enters the pressure-sealed chamber 7 to flow further through the liquid level control means 8 along the pipe 21 through the non-return valve 22, distributor 20 of the gas-steam and gas-liquid flows along the pipe 23 via the valve 24 to enter the inoculator 3. Subsequent to complete or partial (depending on the aim to be attained) displacement of the extract from the steam generator 5 to the bioreactor 1, pressure-sealed chamber 7 and inoculator 3, the valves 18 and 24 are closed, and the valves 12 and 13 are opened for the pressure inside the apparatus to equalize with the atmospheric by means of the pressure regulator 15. The apparatus is cooled by feeding a cooling agent to the heat transfer jacket 29 of the bioreactor 1 and to the heat transfer jacket 34 of the inoculator 3.

In this manner the conditions of sterilization are maintained by circulating steam and steam-liquid mixture along the pipes 9, 16, 23 and 26 and other units of the apparatus in a closed volume, which enables, along with sterilization of the vegetal raw material, to execute pre-treatment thereof residing in softening the vegetal raw material, to obtain the necessary quantity of extracts for subsequently growing thereon of the inoculum, and to prevent compaction of the vegetal raw material while maintaining its initial structure.

Inoculum, such as mycelium fungi *Panus tigrinus* - 144, is introduced to the extract occupying the inoculator 3 through the pipe 36, for which purpose, without disturbing the aseptic conditions in the inoculator 3, the cover cap 37 is removed from the pipe 36.

If necessary, additional nutrient solutions may be introduced to the inoculator 3.

For carrying out the process of growing the inoculum, a corresponding program is preset at the control unit 6, which ensures that the necessary conditions of stirring, temperature controlling and aeration for the growth of the mycelium fungi in the inoculator 3 are maintained. Stirring of the culture suspension formed in the inoculator 3 subsequent to introducing the mycelium is done by rotating the stirrer 35 at a predetermined speed, and temperature controlling is effected by pumping through the heat transfer jacket 34 a heat-transfer agent at a preselected temperature. Aeration is done in a pulsewise manner, wherefor a predetermined pressure of air delivered from the compressed air source is preset at the pressure regulator 15, while duration of cycles required for intermittent actuation of the valves 11 and 12 is preset by the program of the control unit 6.

Therewith, compressed air is delivered from the compressed air source 4 along the pipe 9 via the valve 11, bacterial filter 10 and valve 13 to the inoculator 3 to increase the pressure of air therein to a preset value. Thereafter, the valve 11 is closed and the valve 12 is opened for part of such air to be conveyed from the inoculator 3 along the pipe 9 via the valve 13, bacterial filter 10, valve 12 and pressure regulator 15 to escape to the atmosphere while maintaining in the inoculator the pressure of air as preset by the pressure regulator 15. Subsequently, the cycles for delivering the aerating air to and discharging it from the inoculator 3 are repeated.

Upon the inoculator 3 attaining a predetermined concentration of the mycelium biomass, the thus obtained inoculum is introduced to the vegetal raw material occupying the bioreactor 1, and a program for carrying out the process of bioconversion of the vegetal raw material is preset at the control unit 6.

For realization of this program the control unit 6 generates signals applied to the valves 13, 17, 24, 27 and 40. The thus programmed response of these valves assures intermittent introduction of the inoculum to the entire volume of the vegetal raw material, displacement of liquid from the bioreactor 1 and accumulation thereof in the chamber 7, moistening of the vegetal raw material thereby, and replenishing the volume of the inoculator 3 by the liquid delivered from the chamber 7. Introduction of the inoculum to the vegetal raw material and uniform distribution of the inoculum throughout the body of this material is accomplished in that along with each valve 27 there are opened valves 11, 24 and the valve 17 in antiphase. Aerating air is conveyed from the compressed air source 4 along the pipe 9 through the valve 11, filter 10 and valve 13 to the inoculator 3 to force the inoculum from the inoculator 3 along the pipe 23 through the valve 24 to the distributor 20 of gas-steam, gas-liquid and inoculum flows. Thereafter, the inoculum is introduced to the vegetal raw material along one of the pipes 26 through the open valve 27 and holes 30 of the corresponding feeder 25. At the same time, the compressed air flows through the filter 10 along the pipe 9 to the chamber 7, wherefrom it is conveyed through the liquid level control means 8 along the pipe 21 and via the non-return valve 22 to the flow distributor 20 to travel further along the pipe 26 and through the open valve 27 to the corresponding feeder 25, which provides for spraying of the inoculum from the holes 30 and aeration of the fungi mycelium.

The inoculum delivered to the bioreactor 1 acts to displace from the vegetal raw material excess liquid, which is forced together with spent air in the form of a gas-liquid flow along the pipe 16 and through the valve 17 to the pressure-sealed chamber 7, where the liquid and spent air are separated, the air escaping to the atmosphere through the pipe 9 via the filter 10, valve 12 and pressure regulator 15. The liquid level control means 8 is mounted inside the pressure-sealed chamber 7 at a preselected height to provide in the bioreactor 1 a required moisture content and withdraw heat. In order to replenish the working volume of the inoculator 3 with liquid, the liquid level control means 8 is immersed in the liquid occupying the chamber 7. Without terminating the cyclic aeration, the valves 13 and 27 are temporarily closed, whereby the liquid is forced from the pressure-sealed chamber 7 by compressed air flowing through the liquid level control means 8 along the pipe 21, and through the non-return valve 22 toward the flow distributor 20, wherefrom it is conveyed along the pipe 23 through the valve 24 to the inoculator 3.

The process of bioconversion of the vegetal raw material may be carried out in the proposed apparatus either by periodically introducing the inoculum to the bioreactor 1 and adding liquid to the inoculator 3 or by adding the inoculum to the vegetal raw material in a single-batch manner.

The periodic introduction of the inoculum by spraying it in various points of the body of the vegetal raw material, as well as circulation of liquid for moistening this material and providing for its heat- and mass-transfer ensure homogeneous growth of fungi mycelium in the entire volume of the vegetal raw material subjected to bioconversion, which in turn results in improved efficiency of the apparatus.

To complete the process of bioconversion, the supply of compressed air is terminated, the pressure inside the apparatus is equalized with the atmospheric, the cover plate is removed from the bioreactor 1, and the container 2 with the finished product is withdrawn from the bioreactor 1.

The apparatus can be sterlized without sterilization of the inoculator 3, for which purpose the valve 13 is closed and the valve 40 is opened. While preserving the aseptic conditions necessary for growing the inoculum, the inoculator 3 is communicated with the atmosphere by way of the pipe 37 through the bacterial filter 39 and valve 40.

As distinct from the prior art apparatuses, the entire volume of the bioreactor subjected to heat- and mass-transfer without the use of mechanical stirrers results in increased efficiency of the apparatus, reduced amount of energy consumed for its operation, and less quantity of metal used for the fabrication of the apparatus.

What is claimed is:

1. An apparatus for bioconversion of vegetal raw material comprising:
    a bioreactor;
    a means for charging said bioreactor with vegetal raw material and discharging the end product and communicating with said bioreactor;
    an inoculator communicating with said bioreactor;
    a source of compressed air communicating with said bioreactor;
    a steam source communicating with said bioreactor;
    said compressed air source, inoculator and steam source producing gas-steam, a flow of inoculum and gas-liquid flow;
    a pressure-sealed chamber for storing excess liquid displaceable from said bioreactor and communicating with said compressed air source, inoculator, steam source and bioreactor;
    a liquid level control means disposed inside said pressure-sealed chamber;
    a first pipe for conveying gas-steam flows and communicating said pressure-sealed chamber to the compressed air source;
    a first valve provided in said first pipe;
    a second pipe for conveying gas-steam flows and communicating said pressure-sealed chamber to the atmosphere;
    a second valve provided in said second pipe;

a third pipe for conveying gas-steam flows and communicating said pressure-sealed chamber to said inoculator;
a third valve provided in said third pipe;
a fourth pipe for conveying gas-steam flows and communicating said pressure-sealed chamber to said steam source;
a fourth valve provided in said fourth pipe;
a fifth pipe for conveying gas-liquid flows and communicating said pressure-sealed chamber to said bioreactor;
a fifth valve provided in said fifth pipe;
a sixth pipe for conveying gas-liquid flows and communicating said pressure-sealed chamber to said steam source;
a sixth valve provided in said sixth pipe;
a distributor of said gas-steam, gas-liquid flows and the flow of inoculum connected to said liquid level control means and said inoculator;
a seventh pipe communicating said distributor of gas-steam, gas-liquid flows and the flow of inoculum to said liquid level control means;
a non-return valve provided in said seventh pipe;
an eighth pipe communicating said flow distributor to said inoculator;
a seventh valve provided in said eighth pipe;
a plurality of feeders arranged inside said bioreactor at different levels in terms of height thereof;
pipes equal in number to the number of said feeders and connecting said feeders to said flow distributor;
valves provided in said pipes and equal in number to the number of said pipes connecting said feeders to said flow distributor;
a pump arranged between said bioreactor and said steam source for circulating said gas-steam and gas-liquid flows; and
a control unit having a first output connected electrically to said first valve, a second output connected to said second valve, a third output connected to said third valve, a fourth output connected to said fourth valve, a fifth output connected to said fifth valve, a sixth output connected to said sixth valve, a seventh output connected to said seventh valve, an eighth output connected to said pump, a group of outputs connected to said valves provided in said pipes connecting said feeders to said distributor of gas-steam, gas-liquid flows and the flow of inoculum, and said control unit generating signals to open and close said valves and to energize and deenergize said pump for circulating and blocking said gas-steam, gas-liquid flows and the flow of inoculum.

2. An apparatus as defined in claim 1 wherein each of said feeders is fashioned as a tube having radially extending holes provided on an end thereof immersible in said bioreactor; and further comprising a cover cap plugging said feeder at said end thereof.

3. An apparatus as defined in claim 1 wherein said means for charging the vegetal raw material and discharging the end product is fashioned as a container installed inside said bioreactor and has perforated walls and bottom for preventing compaction of the vegetal raw material by said gas-steam, gas-liquid flows and the flow of inoculum admitted thereto through said feeders, the cross-sectional area of said perforations being smaller than the size of particles of said vegetal raw material.

4. An apparatus as defined in claim 2 wherein said means for charging the vegetal raw material and discharging the end product is fashioned as a container installed inside said bioreactor and has perforated walls and bottom for preventing compaction of the vegetal raw material by said gas-steam, gas-liquid flows and the flow of inoculum admitted thereto through said feeders, the cross-sectional area of said perforations being smaller than the size of particles of said vegetal raw material.

* * * * *